United States Patent [19]

Matkovich et al.

[11] Patent Number: 5,622,626
[45] Date of Patent: Apr. 22, 1997

[54] MULTIPLE COMPARTMENT FILTER AND METHOD FOR PROCESSING PARENTERAL FLUID

[75] Inventors: Vlado I. Matkovich, Glen Cove; Samuel T. Wortham, Huntington; Thomas J. Bormann, Melville, all of N.Y.

[73] Assignee: Pall Corporation, East Hills, N.Y.

[21] Appl. No.: 227,875

[22] Filed: Apr. 15, 1994

[51] Int. Cl.⁶ .................. B01D 29/50; B01D 35/00; B01D 61/00; A61M 1/00
[52] U.S. Cl. .................. 210/649; 210/420; 210/428; 210/435; 210/436; 210/472; 210/650; 210/767; 604/4
[58] Field of Search .................. 210/645, 649, 210/650, 767, 232, 321.6, 420, 428, 435, 436, 455, 472, 484, 340, 341; 604/4, 5, 6, 28, 30; 96/6

[56] References Cited

U.S. PATENT DOCUMENTS

| | | | |
|---|---|---|---|
| 3,803,810 | 4/1974 | Rosenberg . | |
| 3,868,322 | 2/1975 | Orloff | 210/108 |
| 4,177,149 | 12/1979 | Rosenberg | 210/436 |
| 4,223,695 | 9/1980 | Muetterties | 137/173 |
| 4,294,594 | 10/1981 | Sloane, Jr. et al. | 210/436 |
| 4,326,957 | 4/1982 | Rosenberg | 210/436 |
| 4,478,714 | 10/1984 | Blake et al. | 210/136 |
| 4,525,182 | 6/1985 | Rising et al. | 210/436 |
| 4,568,366 | 2/1986 | Frederick et al. | 210/436 |
| 4,655,754 | 4/1987 | Richmond et al. | 604/323 |
| 4,702,840 | 10/1987 | Degen et al. | 210/638 |
| 4,838,858 | 6/1989 | Wortham et al. | 604/83 |
| 4,863,590 | 9/1989 | Ohnishi et al. | 210/340 |
| 4,886,528 | 12/1989 | Aaltonen et al. | 55/270 |
| 4,906,260 | 3/1990 | Emheiser et al. | 210/436 |
| 4,925,572 | 5/1990 | Pall | 210/767 |
| 4,954,256 | 9/1990 | Degen et al. | 210/490 |
| 5,126,054 | 6/1992 | Matkovich | 210/641 |
| 5,176,828 | 1/1993 | Proulx | 210/341 |
| 5,190,524 | 3/1993 | Wex | 604/80 |
| 5,229,012 | 7/1993 | Pall et al. | 210/767 |
| 5,252,222 | 10/1993 | Matkovich et al. | 210/436 |
| 5,296,137 | 3/1994 | Gershon et al. | 210/435 |
| 5,344,392 | 9/1994 | Senninger et al. | 604/4 |

FOREIGN PATENT DOCUMENTS

| | | |
|---|---|---|
| 0333119 | 9/1989 | European Pat. Off. . |
| 0358963 | 3/1990 | European Pat. Off. . |
| 0358964 | 3/1990 | European Pat. Off. . |
| 9117809 | 11/1991 | WIPO . |
| 9322029 | 11/1993 | WIPO . |

*Primary Examiner*—John Kim
*Attorney, Agent, or Firm*—Leydig, Voit & Mayer

[57] ABSTRACT

Methods and devices are disclosed for passing a first parenteral fluid through a first fluid flow path through a fluid treatment arrangement, passing a second parenteral fluid through a separate and isolated second fluid flow path through the fluid treatment arrangement, and passing the first parenteral fluid through the separate and isolated second fluid flow path through the fluid treatment arrangement.

42 Claims, 6 Drawing Sheets

MULTIPLE COMPARTMENT FILTER AND METHOD FOR PROCESSING PARENTERAL FLUID

TECHNICAL FIELD

This invention relates to the processing of fluids, particularly to the filtration of at least one parenteral fluid.

BACKGROUND OF THE INVENTION

Many fluids, particularly those to be administered to a patient, include undesirable or deleterious material that should be removed before the fluid is used for an intended purpose. For example, a parenteral fluid, that is, a fluid that is administered via a pathway other than through the alimentary canal, may include potentially pathogenic microorganisms, such as, for example, bacteria, that should not be administered to a patient. The parenteral fluid may include pyrogenic substances and/or particulate matter that should be removed before using the fluid.

Since the administration of a parenteral fluid including an undesirable material to a patient may cause an adverse effect, e.g., fever, in the patient receiving this fluid, it may be advisable to process the fluid to remove this material. Typically, a parenteral fluid is passed through a device including a porous medium to remove undesirable or deleterious matter. In some protocols, e.g., involving continuous and/or long term administration, different parenteral fluids are administered, and each fluid may be passed along the same flow path through the porous medium to remove this matter. For example, a patient receiving fluid replenishment, e.g., a continuous saline drip, may periodically require medicaments and/or nutrients, and each of these fluids may be passed through the same flow path through the porous medium.

However, there may be a number of drawbacks associated with some of the protocols summarized above. For example, while passing the fluid(s) through a porous medium may remove the undesirable material, this may also cause the loss of some of the parenteral fluid. For example, valuable parenteral fluid may be held up in the porous medium and/or the housing containing the porous medium. Fluid may be lost to the medium, e.g., due to absorption by the medium. As a result, this held up or lost fluid may be essentially unavailable to the patient, or may have to be flushed through the device by a carrier fluid, to be administered in the amount intended. The time required to flush this additional fluid may delay administration of the intended dose (e.g., a bolus dose) of the parenteral fluid. Additionally, in some situations, particularly those involving administration of precise amounts of fluid, it may be difficult to accurately administer the correct amount of filtered fluid. The problem may be magnified when only a small volume of fluid is to be administered.

There are other problems associated with the use of a single flow path passing through the same porous medium when processing parenteral fluids. For example, the same porous medium may not be suitable or equally efficient for processing different parenteral fluids. Thus, a porous medium suitable for passing a parenteral fluid such as saline may be less suitable for passing a different parenteral fluid, such as a parenteral fluid including an emulsion, e.g., a nutrient solution or an anesthetic.

Furthermore, it may be awkward and/or time consuming to add another parenteral fluid line, e.g., by "piggybacking." Additionally, properly controlling the flow paths and/or flow rates of the various fluids may be labor intensive.

Also, when processing and/or administering fluids, it may be desirable to minimize the presence of, or interference by, air or gas. For example, particularly in those protocols involving processing of small volumes of fluid, it may be difficult to pass a liquid through a porous medium if air is present, since the air may block the porous medium. Also, since air should not be administered to a patient, it may be desirable to minimize the presence of air, e.g., by venting the gas from the fluid treatment device that includes the porous medium.

Accordingly, there is an unanswered need in the art for a method, device and system for efficiently processing a fluid, particularly a parenteral fluid, to remove undesirable material. There is also a need for a method, device and system for efficiently processing different parenteral fluids. Preferably, different parenteral fluids may be processed so that air or gas may be separated from the parenteral fluids and/or so that the fluids may be efficiently processed while air is present.

Moreover, there is also a need for a device, system and method for processing a fluid that provides for increasing the amount of fluid available for an intended use, for example, for administration to a patient.

These and other advantages of the present invention will be apparent from the description as set forth below.

SUMMARY OF THE INVENTION

Processes, devices and systems according to the instant invention provide for processing at least one fluid, more preferably, at least two fluids, by passing the fluid(s) through isolated fluid flow paths through a fluid treatment arrangement. Preferably, each of at least two parenteral fluids are passed through a separate and isolated flow path through a fluid treatment arrangement and, if undesirable material is present in at least one of the fluids, this material is removed by passing the fluid(s) through the fluid treatment arrangement. The two parenteral fluids may then be passed through a common fluid path downstream of the fluid treatment arrangement.

In accordance with the invention, different parenteral fluids may be quickly and efficiently processed and administered to a patient. In view of the expense of various parenteral fluids, particularly medicament and/or nutrient containing parenteral fluids, the present invention is especially advantageous in that it minimizes the loss and/or hold up of valuable parenteral fluids, e.g., in the fluid treatment arrangement and/or housing, during processing. For example, two or more parenteral fluids such as a carrier fluid and a therapeutic fluid, e.g., a fluid including a medicament and/or a nutrient, may be passed through separate and isolated flow paths through a fluid treatment arrangement, while minimizing the volume of medicament and/or nutrient containing fluid that is held up in the fluid treatment device and/or absorbed by the fluid treatment arrangement. This is especially desirable in those embodiments including administering parenteral fluid to a smaller patient, e.g., a neonatal human or animal.

In accordance with the invention, small volumes of medicament and/or nutrient containing fluids may be efficiently processed and administered in accurate amounts, which provides safety benefits in addition to the cost savings resulting from minimizing the loss of expensive fluid. Moreover, since different fluids may be quickly and easily processed, the present invention is particularly useful in those protocols involving long term or continuous administration of one parenteral fluid along with short term and/or intermittent administration of a different parenteral fluid.

In accordance with the invention, the fluid treatment arrangement is easily and quickly primed to provide for effective fluid processing. The processes, devices and systems of the present invention also provide for efficient fluid processing when air is present. Preferably, the instant invention provides for separating gas from a parenteral fluid, regardless of the position of the parenteral fluid treatment device.

SPECIFIC DESCRIPTION OF THE INVENTION

Figure 1:
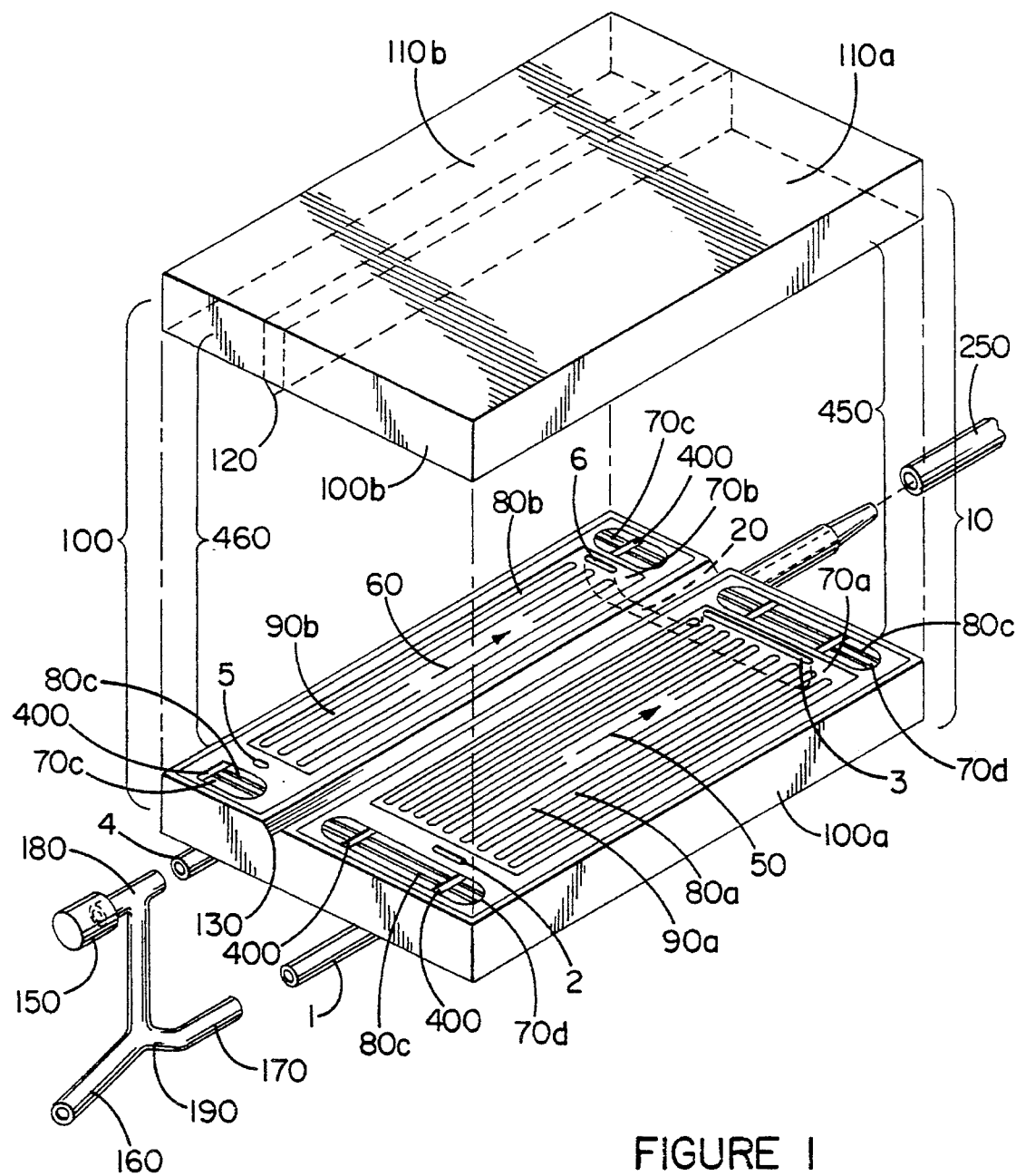
FIG. 1 is an oblique view of a housing of a device according to the present invention.

The present invention includes a method for treating parenteral fluid comprising passing a first parenteral fluid through a first fluid flow path through a fluid treatment arrangement; passing a second parenteral fluid through a separate and isolated second fluid flow path through the fluid treatment arrangement; and, passing first fluid through the separate and isolated second fluid flow path through the fluid treatment arrangement. Gas may be displaced from the flow paths of the first and second parenteral fluids. In a preferred embodiment, less parenteral fluid is held up in one fluid flow path than in the other fluid flow path.

A method for processing parenteral fluid is provided comprising passing a carrier fluid through a first fluid flow path through a fluid treatment arrangement; and, passing a therapeutic fluid including a lipid in emulsion, said therapeutic fluid being compatible with the carrier fluid, through a separate and isolated second fluid flow path through the fluid treatment arrangement.

In accordance with the invention, an apparatus for processing a parenteral fluid is provided comprising a housing, a fluid treatment arrangement within the housing, said housing providing for at least a first fluid flow path from a first inlet through the fluid treatment arrangement and through a first outlet, and a separate second fluid flow path from a second inlet through the fluid treatment arrangement and through a second outlet; said fluid treatment arrangement being interposed across the first fluid flow path and the separate second fluid flow path, and having a larger effective flow area in the first fluid flow path than in the second fluid flow path.

The present invention provides an apparatus for processing a parenteral fluid comprising a fluid treatment arrangement including at least one porous medium; a housing providing for at least a first fluid flow path from a first inlet through the fluid treatment arrangement and through a common outlet, and a separate second fluid flow path through a second inlet through the fluid treatment arrangement and through the common outlet, wherein the fluid treatment arrangement is located within the housing, across the first fluid flow path and the separate second fluid flow path.

The present invention also provides an apparatus for processing parenteral fluid comprising a housing including at least a first subassembly and a second subassembly, said housing providing for at least a first fluid flow path through the first subassembly and a separate and isolated second fluid flow path through the second subassembly, said first subassembly having a larger fluid hold up volume than said second subassembly; and, a fluid treatment arrangement located within the first subassembly and the second subassembly, said arrangement interposed across the first fluid flow path and the separate and isolated second fluid flow path.

In accordance with the invention, a device for processing a parenteral fluid comprises a housing including a first portion and a second portion, said first portion including a groove; said second portion including a spacer capable of fitting into the groove, wherein said housing provides first and second isolated fluid flow paths when said spacer fits in said groove.

As used herein, a parenteral fluid is a physiologically acceptable fluid. The parenteral fluid may be used in prophylactic and/or existing condition treatment protocols. In a preferred embodiment, a parenteral fluid refers to at least one of a carrier fluid, and a therapeutic fluid. The parenteral fluid may be a sterile fluid.

A carrier fluid, also referred to as a maintenance fluid, is preferably suitable for combining and/or commingling with another parenteral fluid, for example, a therapeutic fluid, such as a fluid containing a medicament or a nutrient. Typical carrier or maintenance fluids include those used in re-hydration or fluid replenishment protocols. Other suitable carrier fluids include those used to flush therapeutic fluids and/or agents that are held up in components of parenteral fluid processing systems, e.g., in a filter and/or conduit, into a patient. In some embodiments, the carrier fluid may also be a therapeutic fluid. Exemplary carrier fluids include, but are not limited to one or more of a saline solution, for example, an isotonic (about 0.9%) sterile saline solution; an electrolyte solution, including, for example, dextrose 5% in water (D5W); an albumen solution or suspension; and a preservative solution, for example, benzalkonium chloride. It is intended that the present invention is not to be limited by the carrier fluid used.

The therapeutic fluid typically includes a medicament and/or a nutrient. The medicament and/or nutrient may be soluble in water, or insoluble in water. Non-soluble nutrient and/or medicament containing parenteral fluids typically include emulsions, preferably oil-in-water emulsions, and may include molecules such as lipids. The medicament and/or nutrient may include micelies. In a preferred embodiment, a medicament including fluid includes at least one drug. Exemplary drugs include, but are not limited to antibiotics, e.g., gentamicin, vancomycin, and cephalosporin; antifungals; insulin; digitalis; nitroglycerine; anesthetics, e.g., propofol; and cytotoxic drugs. The medicament including drug may comprise a solution including a drug, e.g., digitalis, or an emulsion including a drug, e.g., propofol and amphotericin B. Suitable fluids containing nutrients include, for example, total nutrient admixtures (TNAs), total parenteral nutrient (TPN) admixtures, amino acids, and vitamins. It is intended that the present invention is not to be limited by the therapeutic and/or medicinal fluid.

The parenteral fluids of the present invention e.g, carrier fluids and/or therapeutic fluids, may also include any of a number of other substances, including, but not limited to, emulsifying agents, stabilizers, and trace elements. It is intended that the present invention is not to be limited by the number, amount, or type of these other substances.

Preferably, the invention includes processing two or more parenteral fluids, more preferably, two or more intravenous fluids. For example, the invention includes the use of a carrier fluid such as saline as one intravenous fluid, and a therapeutic fluid including a medicament and/or a nutrient as another intravenous fluid. The invention also includes the use of a first therapeutic fluid including a medicament and/or a nutrient, and a second therapeutic fluid including a different medicament and/or nutrient.

Preferably, when two or more fluids are utilized, the fluids are compatible with one another, and may be commingled and/or mixed in accordance with the invention, if desired. As used herein, compatibility refers to an intended use, and may encompass interactions between the fluids. For example, two or more fluids may interact with each other chemically, and still be suitable for an intended use, e.g., administration to a patient.

The fluid or fluids may also include a number of undesirable materials. The undesirable elements may be present in the fluid as a result of the storage condition or environment, normal metabolic processes, or due to the processing environment, or other causes. The undesirable material may be a biological or a non-biological substance. As used herein, undesirable material refers to microorganisms, e.g., bacteria and/or fungi, as well as particulate, chemical, and other substances or impurities which are preferably removed or depleted from the fluid. Exemplary undesirable materials include but are not limited to particulates, and the like, typically, but not limited to coalesced particles, precipitates, pyrogenic matter such as bacterial endotoxins, emboli, administration set contaminants such as ampule and vial material, e.g., glass shards, septa bits, and the like. It is intended that the present invention is not to be limited by the type of undesirable material removed.

In an exemplary device embodying the present invention, at least one fluid treatment arrangement including one or more fluid treatment elements is located within a housing so as to provide two or more separate fluid flow paths between the inlet(s) and the outlet(s) of the housing. Preferably, two or more separate and isolated flow paths through a fluid treatment arrangement including two or more fluid treatment elements are provided.

Preferably, the housing is configured to minimize the fluid hold up in or along at least one of the isolated flow paths. In another preferred embodiment, the fluid treatment arrangement within the housing provides for minimizing the amount of fluid "lost" to the medium and/or the housing, e.g., due to absorption, as the fluid passes along at least one of the isolated flow paths. In a more preferred embodiment, the housing includes two or more subassemblies, and each subassembly includes a chamber on the upstream side of a fluid treatment element, and the housing includes a wall or spacer between the chambers to seal or divide one fluid flow path from another.

In a preferred embodiment, the housing is formed from a material that is substantially impermeable to, and substantially unreactive with, the fluids and liquids processed in accordance with the invention, and the fluid processing apparatus is configured such that the flow paths are separated and isolated from each other by this substantially impermeable and unreactive material.

A variety of housing configurations and shapes are suitable for providing two or more separate fluid flow paths through a fluid treatment arrangement. For example, the device may include two or more inlets and/or two or more outlets. Inlets and/or outlets may be associated with opposite surfaces of the fluid treatment arrangement. Additionally, the housing may be circular, triangular, rectangular or square in shape.

Preferably, the apparatus comprises a housing including two or more inlets, a fluid treatment arrangement including two or more fluid treatment elements, and a common outlet. The apparatus may include two or more subassemblies.

As illustrated in FIGS. 1, 2, 5 and 6, a preferred fluid processing device or apparatus 10 according to the invention comprises a housing 100 having first and second portions 100a, 100b joined in any convenient manner.

In the illustrated embodiments of FIGS. 1, 2, 5 and 6, the housing 100 includes a first fluid inlet 1, a second fluid inlet 4, a fluid treatment arrangement 200 including first fluid treatment element 200a and second fluid treatment element 200b, and an outlet 20. First fluid inlet 1 communicates with first fluid entry port 2, and second fluid inlet 4 communicates with second fluid entry port 5. First subassembly 450 includes first fluid entry port 2 which communicates with one side of the first fluid treatment element 200a, and first fluid exit port 3 which communicates with the other side of the first fluid treatment element 200a, to establish first fluid flow path 50 through the first fluid treatment element 200a. Second subassembly 460 includes second fluid entry port 5 which communicates with one side of the second fluid treatment element 200b, and fluid exit port 6 which communicates with the other side of second fluid treatment element 200b, to establish second fluid flow path 60 through the second fluid treatment element 200b. In these embodiments, and as will be noted in more detail below, first fluid flow path 50 is preferably separate and isolated from second fluid flow path 60.

Figure 5:
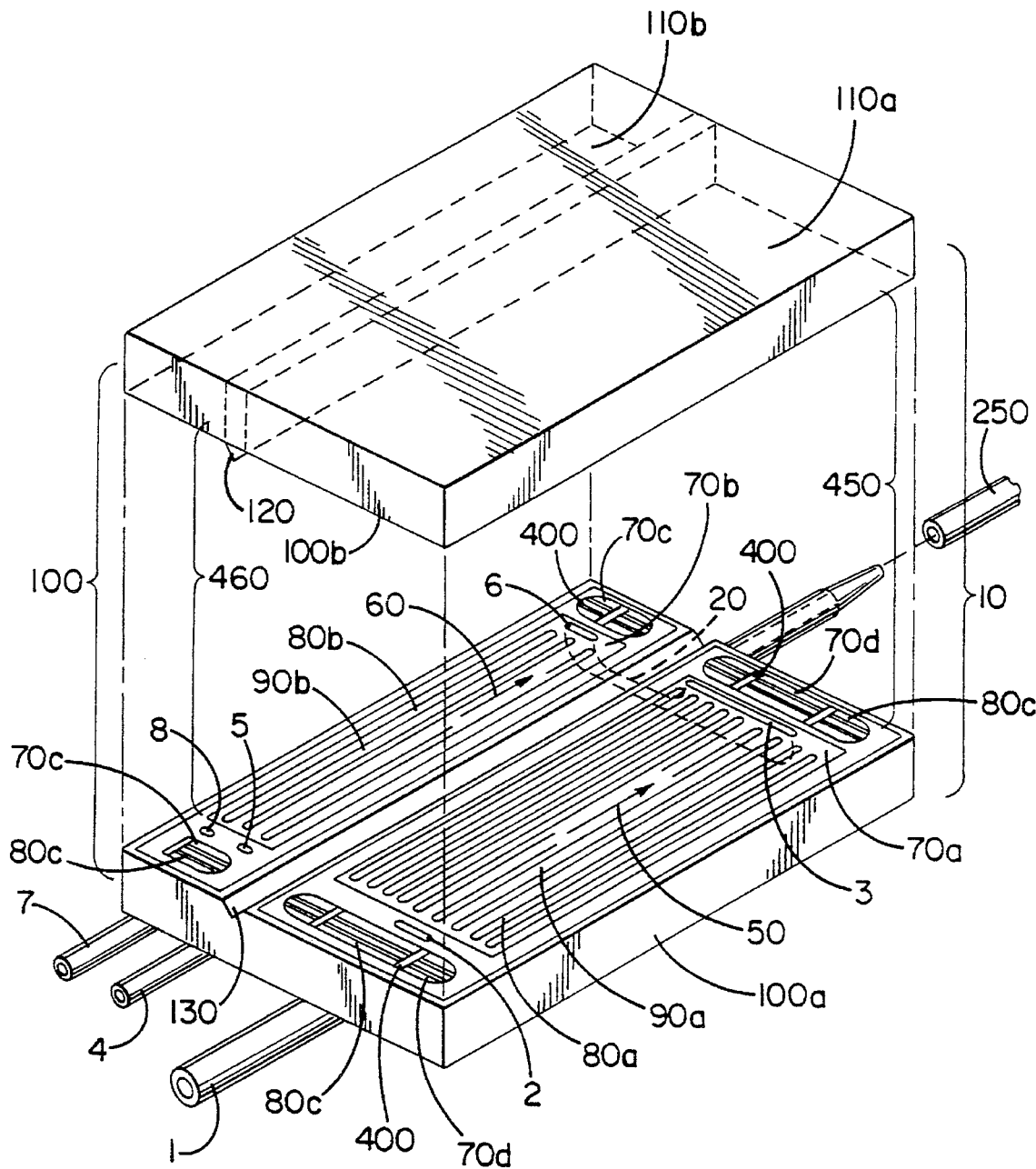
FIG. 5 is an oblique view of another embodiment of the present invention.
Figure 6:
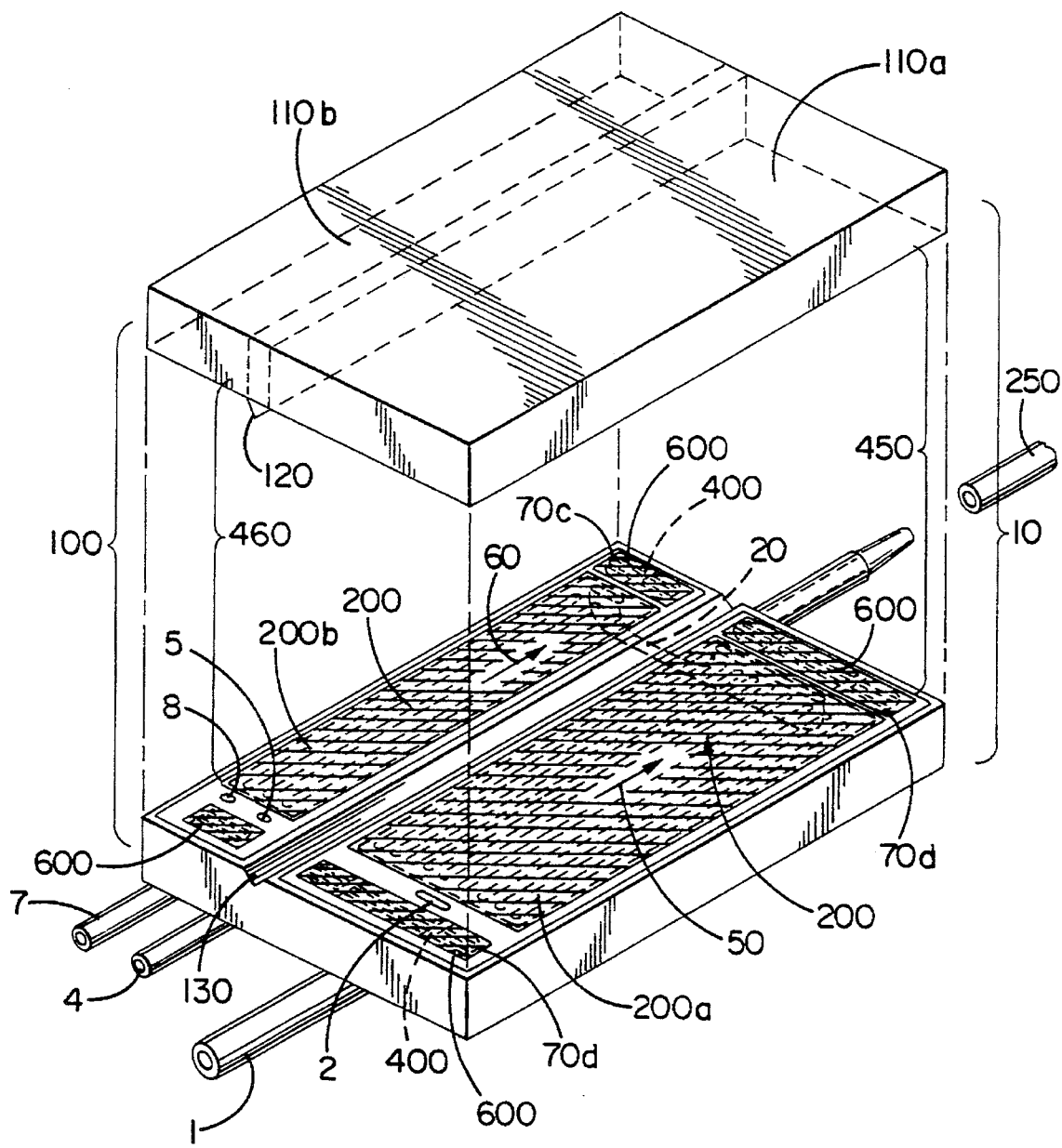
FIG. 6 is a view of a device according to the present invention including the housing of FIG. 5 and a fluid treatment arrangement and a venting element.

The embodiment illustrated in FIGS. 5 and 6 includes an additional inlet, supplementary fluid inlet 7, which leads to an additional entry port, supplementary entry port 8. Typically, supplementary fluid inlet 7 is an injection fluid inlet and/or an infusion fluid inlet. Second subassembly 460 includes second fluid entry port 5 and injection fluid entry port 8 which both communicate with second fluid treatment element 200b and a common fluid exit port, exit port 6, and share second fluid flow path 60. In those embodiments wherein the supplementary inlet 7 is an injection fluid inlet, the inlet is preferably parallel to the plane of the fluid treatment arrangement 200. Among other advantages, this minimizes the possibility that the fluid treatment arrangement will be damaged, e.g., punctured, during injection.

In the embodiments illustrated in, for example, FIGS. 1 and 5, fluid exit ports 3 and 6 lead to common outlet 20, which provides a single common commingling fluid flow path or channel downstream of fluid treatment arrangement 200. The outlet 20 is in fluid communication with a conduit such as single channel conduit 250. The outlet 20 may be integrally connected to the conduit 250.

In another embodiment (not shown), the housing may include separate outlets for the exit ports. Preferably, a connector downstream of the first fluid exit port and the second fluid/supplementary fluid exit port leading to a single conduit provides for a common flow path for the various fluids, so that all of the fluids can share a common flow path downstream of the fluid treatment arrangement.

While fluid flow paths 50 and 60 are preferably separate and isolated from each other, so that liquid and gas flowing along flow path 50 does not enter or pass along flow path 60, and vice versa, fluids may nonetheless be commingled along a single flow path, for example, along flow path 60, since different fluids may be added through inlets 4 and 7, as in, for example, FIGS. 5 and 6.

Other configurations are encompassed by the instant invention. For example, in a preferred embodiment as illustrated in FIG. 1, the fluid processing apparatus 10 includes some components similar to those illustrated in FIG. 5 (like components have like reference numbers), and fluid flow path 50 is separate and isolated from fluid flow path 60. However, this embodiment includes an access port 150 rather than supplementary fluid inlet 7 and supplementary entry port 8. In a preferred embodiment, access port 150 is an injection port. The embodiment shown in FIG. 1 includes an access port 150 such as an injection port upstream of second fluid inlet 4, so that the desired fluid may be added through the port at the appropriate time. For example, the fluid processing apparatus according to this embodiment may be utilized in a system that includes conduits (160, 170, and 180) and a connector 190 such as a Y-connector to provide fluid communication with first fluid inlet 1 and second fluid inlet 4. In the illustrated embodiment, access port 150 is interposed between one of the arms of the connector 190 and the second fluid inlet 4. This embodiment may provide for commingling of fluids to be passed along the fluid flow path 60, since, for example, a different fluid may be added through conduit 160 than added through access port 150.

The housing 100 may include an arrangement of one or more subassemblies, chambers, wells, channels, grooves, conduits, passages, ribs or the like which may be parallel, serpentine, spiral, or curved, or a variety of other configurations to provide for more efficient fluid flow.

In a preferred embodiment, which includes a fluid treatment arrangement 200 including at least one fluid treatment element 200a and/or 200b in the form of a planar sheet, the housing includes ribs facing the downstream side of the fluid treatment element to support the element in the direction of the pressure drop across the element.

In the embodiments illustrated in FIGS. 1 and 5, first housing portion 100a includes portions of first subassembly 450 and second subassembly 460, since first housing portion 100a includes wells or depressions 70a and 70b, as well as ribs 80a and 80b and channels 90a and 90b. In the illustrated embodiment, first subassembly 450 includes well 70a, ribs 80a and channels 90a, and second subassembly 460 includes well 70b, ribs 80b and channels 90b. As will be noted in more detail below, the subassemblies may include additional components, e.g., chambers 110a and 110b, as shown in, for example, FIGS. 2 and 6.

Figure 3:
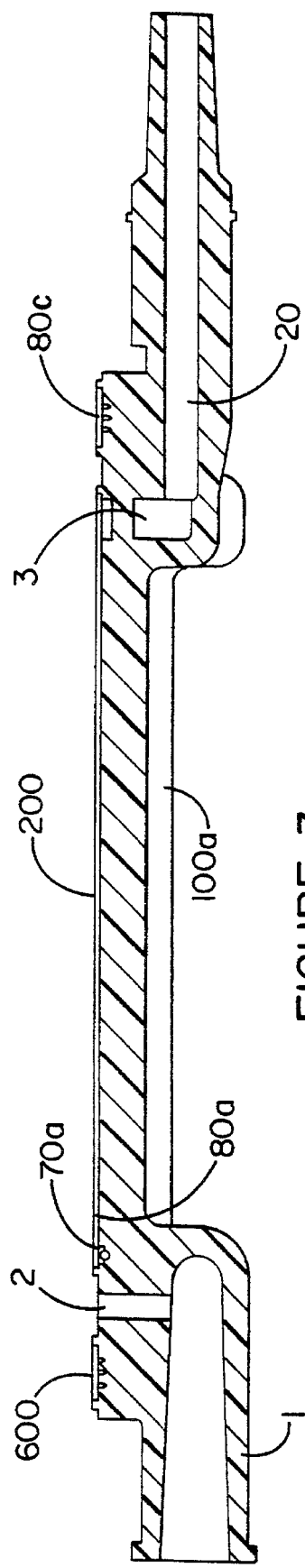
FIG. 3 is a cross-sectional elevated view of the lower portion of the housing taken along the line I—I of the device of FIG. 2.

In a preferred embodiment, the ribs 80a and 80b and the channels 90a and 90b fail to extend beyond the periphery of the respective wells or depressions 70a and 70b, as illustrated in FIGS. 1, 3 and 5. Preferably, the wells and/or channels are as shallow as possible while still allowing sufficient flow of the parenteral fluid(s) through the fluid treatment arrangement 200.

With respect to wells or depressions 70a and 70b, as shown in FIGS. 1, 3 and 5, in a preferred embodiment, exit ports 3 and 6 are located within the periphery of the depressions, and are covered by the fluid treatment arrangement, and inlet ports 2, 5 and 8 are located outside of the periphery of the depressions and are not covered by the fluid treatment arrangement.

In the embodiments illustrated in FIGS. 1, 2, 5 and 6, second housing portion 100b includes portions of first subassembly 450 and second subassembly 460, since second housing portion 100b includes first chamber 110a and second chamber 110b, with spacer 120 separating the chambers. Preferably, first chamber 110a, which is part of first subassembly 450, may be larger (e.g., wider) than second chamber 110b, which is part of second subassembly 460. When first housing portion 110a and second portion 110b are joined, spacer 120 contacts the fluid treatment arrangement 200 such that separate and isolated fluid flow paths through the fluid treatment arrangement are provided, for example, one through the first subassembly 450 and another through the second subassembly 460. In a more preferred embodiment, first housing portion 100a includes a groove 130, so that joining housing portions 100a and 100b allows spacer 120 to fit within groove 130 to form a seal separating the flow paths 50 and 60.

Figure 2:
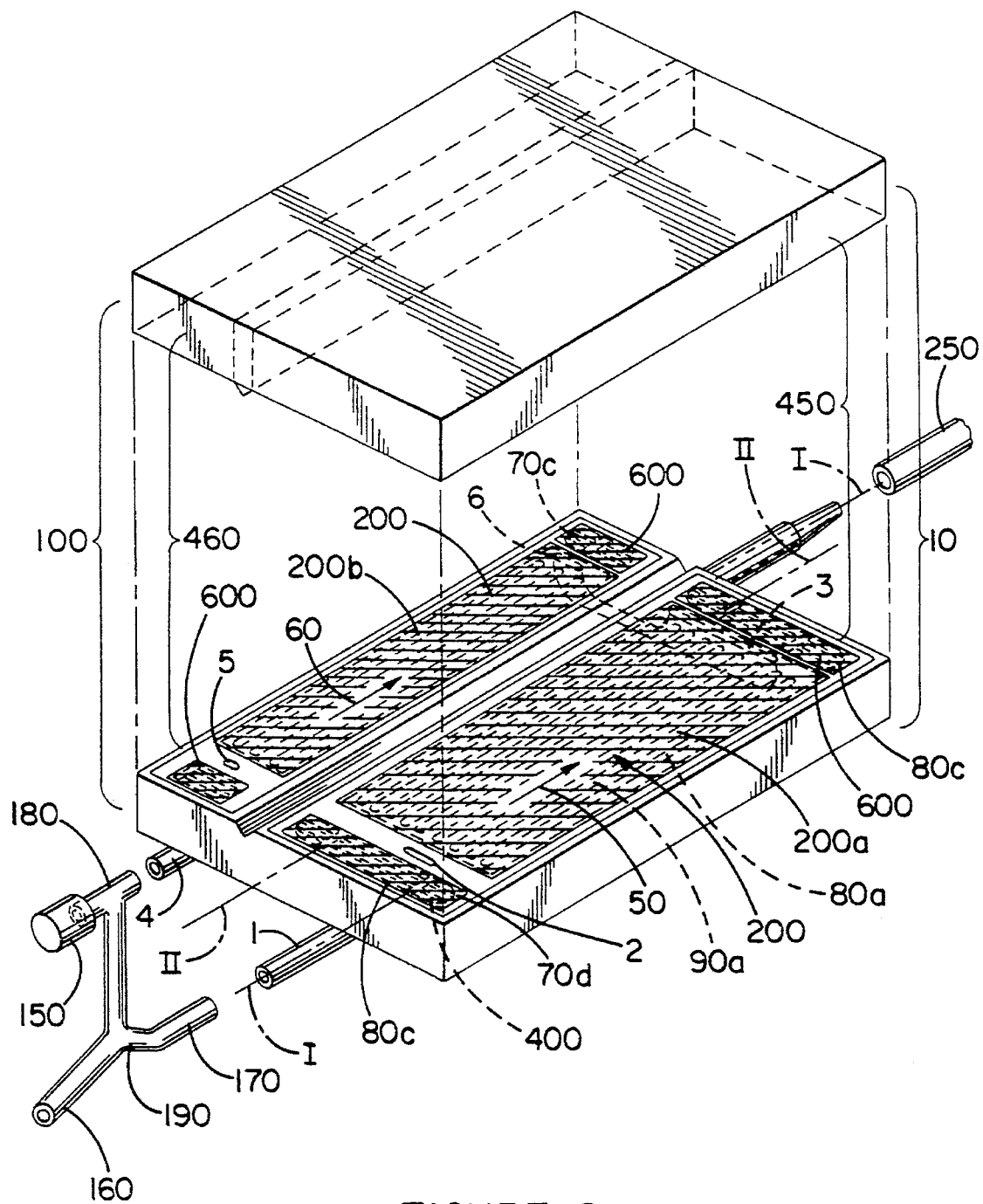
FIG. 2 is a view of a device according to the present invention including the housing of FIG. 1 and a fluid treatment arrangement and a venting element.

In the embodiment illustrated in FIGS. 2 and 6, fluid treatment arrangement 200 includes first fluid treatment element 200a and second fluid treatment element 200b. First fluid treatment element 200a is interposed between first fluid entry port 2 and first fluid exit port 3 as part of first subassembly 450. Second fluid treatment element 200b in FIG. 6 is interposed between second fluid entry port 5 and supplementary fluid entry port 8 on one side and fluid exit port 6 on the other side as part of second subassembly 460. With respect to FIG. 2, second fluid treatment element 200b is interposed between second fluid entry port 5 and fluid exit port 6 as part of second subassembly 460. In a preferred embodiment, as noted in more detail below, first fluid treatment element 200a and second fluid treatment element 200b differ with respect to at least one of, for example, type of medium, dimension (e.g., width, length, and/or thickness), and hold up volume.

Preferably, as illustrated in FIGS. 1 and 5, first subassembly 450 includes first fluid flow path 50, and second subassembly 460 includes second fluid flow path 60. First and second fluid flow paths 50 and 60 passing through first and second fluid treatment elements 200a and 200b, respectively, may be separated from each other in any suitable manner. In the illustrated embodiments, the fluid flow paths are separated from one another by spacer 120 when first and second housing portions 110a and 110b are joined, and spacer 120 seals within groove 130. In the illustrated embodiments, spacer 120 contacts first and second fluid treatment elements 200a and 200b to form a fluid tight seal between the elements 200a and 200b as well as between first and second chambers 110a and 110b and between first and second wells 70a and 70b.

The total fluid hold up volume of the fluid processing apparatus 10 may vary depending on, for example, the fluid(s) processed and the intended use. A typical hold up volume may be in the range from about 0.1 cc to about 4 cc. Preferably, the housing 100 includes a construction that provides for minimizing the volume of fluid held up in the housing, e.g., in at least one subassembly, as the fluid passes along at least one of the isolated fluid flow paths. One construction for minimizing the hold up volume includes minimizing the size or volume of at least one of the subassemblies, typically by minimizing the size or volume of the chambers and/or wells within a subassembly.

In those embodiments including two subassemblies, each subassembly typically has a hold up volume in the range of about 0.1 cc to about 1.5 cc. More preferably, at least one subassembly has a hold up volume of less than about 0.9 cc, even more preferably, less than about 0.7 cc.

In one exemplary embodiment, one of the subassemblies may provide for about 30% of the total hold up volume of the processing apparatus 10, and the other subassembly may provide for about 70% of the total hold up volume. Thus, with respect to an exemplary assembly including a total hold up volume of about 2.0 cc, one subassembly may have a hold up volume of about 0.6 cc, and the other subassembly may have a hold up volume of about 1.4 cc.

In another embodiment, one of the subassemblies may provide for a hold up volume of about 6% of the total hold up volume. Thus, with respect to an exemplary assembly including a total hold up volume of about 2.50 cc, one subassembly may have a hold up volume of about 0.15 cc, and the other subassembly may have a hold up volume of about 2.35 cc.

The fluid treatment arrangement 200, in accordance with the present invention, comprises at least one porous medium suitable for passing at least one fluid, preferably at least two different parenteral fluids, therethrough. More preferably, the fluid treatment arrangement 200 comprises at least one fluid treatment element 200a and/or 200b including at least one porous medium suitable for passing at least one parenteral fluid therethrough while depleting deleterious or undesirable material from the fluid.

As noted above, the fluid treatment arrangement 200 may include two or more fluid treatment elements, e.g., element 200a and element 200b. Each fluid treatment element may comprise at least one porous medium, and the respective fluid treatment elements may differ with respect to particular characteristics or parameters. Elements 200a and 200b may differ with respect to, for example, at least one of type of medium, surface chemistry, width, length, thickness, pore structure, number of layers, hold up volume, and effective flow area, i.e., the face surface area contacted by the fluid. In a more preferred embodiment, second fluid treatment element 200b has a smaller hold up volume and/or effective flow area than that of first fluid treatment element 200a.

The porous medium, which is preferably microporous, may have a substantially uniform pore structure or arrangement, e.g., a uniform pore diameter, or a uniform pore size, or a uniform pore rating. Alternatively, the porous medium may include a pore structure or arrangement that varies in a continuous, discontinuous, or stepwise manner. Having varied pore structure may contribute to lowering the differential pressure, and may permit passing an increased volume of parenteral fluid.

The pore structure may be characterized in terms of pore size, which may be determined by a variety of techniques known to the ordinary artisan. Illustratively, the pore structure may refer to the pore diameter as measured by, for example, the modified F2 test, e.g., as described in U.S. Pat. Nos. 4,925,572 and 5,229,012. The pore structure may refer to an average pore size as measured by, for example, a Coulter porometer II® machine. Other suitable techniques for determining pore structure values include bubble point tests and the use of microorganisms of known size and approximate concentration to challenge the porous medium.

In a preferred embodiment, the porous medium has a pore structure sufficient to block microorganisms and other undesirable substances and allows parenteral fluid to pass through, e.g., a pore size less than about 1.2 micrometers, preferably, less than about 0.8 micrometers, more preferably, in the range of from about 0.45 to about 0.2 micrometers, or less.

Alternatively or additionally, the pore structure may be characterized in terms of a pore rating, e.g., an effective or absolute pore rating, rather than a pore size. In a preferred embodiment, the porous medium includes a pore rating sufficient to block microorganisms and other undesirable substances, e.g., a pore rating of less than about 1.2 micrometers, preferably, in the range of from about 0.45 to about 0.2 micrometers, or less.

As noted previously, pore structure may be determined according to a variety of methods. For example, the pore rating may be determined in accordance with the removal rating of a filtration element or porous medium in terms of measuring its efficiency in removing uniform and/or known substances, e.g., uniform diameter polystyrene microspheres in a liquid medium. For example, the pore rating may be determined using a Latex Sphere Test. Exemplary methods for determining the pore rating utilizing the Latex Sphere Test are disclosed in International Publication No. WO 93/22029, and U.S. Pat. No. 5,252,222.

The fluid filtration arrangement may comprise a porous medium including a single layer. For example, in one embodiment, as illustrated in FIG. 3, fluid treatment arrangement 200 includes a single layer which may include a microorganism blocking pore structure.

A fluid filtration arrangement according to the invention may also include a porous medium having multiple layers, i.e., two or more layers, and/or may include multiple porous media. The different layers and/or media may include different pore structure values.

Although a single pore structure value and/or a single layer may be sufficient for passing a variety of parenteral fluids, in those embodiments wherein extensive and/or finer filtration may be desirable, the fluid treatment arrangement may include different pore structure values and/or different layers, to enhance the filtration. For example, the fluid treatment arrangement may comprise at least two layers, wherein the upstream layer has a coarser pore rating than the downstream layer, wherein at least the downstream pore rating blocks microorganisms and other undesirable material. The fluid treatment arrangement may also include at least one intermediate layer with a pore rating that is finer than that of the upstream layer and coarser that of the downstream layer, or the intermediate layer may have a coarser pore rating than that of the upstream layer.

While the fluid filtration arrangement may be produced from any suitable material compatible with a fluid such as a parenteral fluid, commercially available materials are preferred. The fluid treatment arrangement of this invention may be preferably formed, for example, from any natural or synthetic material capable of forming fibers or a membrane. Suitable polymers include, but are not limited to, polyolefins, polyesters, polyamides, polysulfones, acrylics, polyacrylonitriles, polyaramides, polyarylene oxides and sulfides, and polymers and copolymers made from halogenated olefins and unsaturated nitriles. Examples include, but are not limited to, polyvinylidene difluoride (PVDF), polyethylene, polypropylene, polybutylene terephthalate (PBT), polyethylene terephthalate (PET), and any nylon, e.g., Nylon 6, 11, 46, 66, and 610. Preferred polymers are polyolefins, polyesters, and polyamides. Especially preferred is nylon.

Other suitable materials include cellulosic derivatives, such as cellulose acetate, cellulose propionate, cellulose acetate-propionate, cellulose acetate-butyrate, and cellulose butyrate. Non-resinous materials, such as glass fibers, may also be used.

Exemplary membranes are disclosed in U.S. Pat. No. 4,702,840. Other membranes, including those disclosed in U.S. Pat. Nos. 4,906,374; 4,886,836; 4,964,989; 5,019,260; 4,340,479; 4,855,163; 4,774,132; 4,707,266; 4,203,848 and 4,618,533, may also be suitable. Fibrous media, for example, those disclosed in U.S. Pat. No. 5,133,878, may also be suitable.

Particularly preferred are commercially available media, such as those available from Pall Corporation under the trademark POSIDYNE®. Commercially available membranes, such as those available from Pall Corporation under the trademarks ULTIPOR $N_{66}$®, ULTIPOR®, FLUORODYNE®, LOPRODYNE®, CARBOXYDYNE®, IMMUNODYNE®, BIODYNE A®, BIODYNE B®, BIODYNE C®, as well as commercially available fibrous media, such as those available from Pall Corporation under the trademark HDC® may also be suitable.

In those embodiments wherein the fluid treatment arrangement comprises at least one fluid treatment element including a membrane, the membrane may comprise a microporous membrane, more preferably a skinless microporous membrane. A microporous membrane, as the term is used herein, refers to a thin sheet, generally formed from a synthetic plastic material, having a continuous matrix structure containing myriad pores typically ranging from a few micrometers to about 0.04 micrometers in diameter.

In those embodiments wherein the fluid treatment arrangement comprises at least one fluid treatment element including a fibrous medium, the fibrous medium may comprise a fibrous matrix, more preferably, a microfibrous matrix, such as, for example, a synthetic, polymeric microfibrous matrix. A microfibrous matrix, as the term is used herein, indicates a sheet-like web, or a three-dimensional network of fibers, whether melt-blown, staple, or continuous, which together form a coherent structure suitable for use as a filter medium. Preferred microfibrous matrices are made from melt-blown thermoplastic polymeric fibers, where the fiber diameter is typically in the range of from about 0.5 to about 20 micrometers, more preferably in the range of from about 1 to about 4 micrometers.

The fluid treatment arrangement may remain untreated, or the fibers or membrane may be treated to increase its effectiveness. There are a number of methods for treating the fluid filtration arrangement or fluid treatment element to increase its effectiveness. For example, the fibers and/or the membrane may be surface modified to provide a low affinity for amide or peptide group-containing materials, particularly proteinaceous materials. The fibers and/or the membrane may be surface modified to affect the critical wetting surface tension (CWST) of the element. The fibers and/or the membrane may be treated to inactivate (e.g., prevent multiplication) and/or kill microorganisms.

The fibers and/or membrane may be modified with a charge modifying agent to produce a negatively or positively charged medium, and/or a negative or positive zeta potential. The fibers and/or the membrane may be charge neutral. Preferably, in those embodiments including the removal of endotoxins and/or bacteria from the fluid, the porous medium includes a positive zeta potential.

Surface characteristics of a fiber and/or membrane can be modified by chemical reaction including wet or dry oxidation, by coating or depositing a polymer on the surface, or by a grafting reaction. Grafting reactions may be activated by exposure to an energy source such as gas plasma, heat, a Van der Graff generator, ultraviolet light, or to various other forms of radiation, or by surface etching or deposition using a gas plasma treatment. The preferred method for a grafting reaction uses gamma-radiation, for example, from a cobalt source. The preferred method for gas plasma treatment uses a low temperature gas plasma. More preferably, the gas plasma is an inorganic gas, for example, oxygen or ammonia. Exemplary techniques for gas plasma treatment include those disclosed in U.S. Pat. No. 5,258,127 and International Publication No. WO 93/04763.

As noted earlier, the fibers and/or membrane may be treated to modify the CWST of the fluid filtration arrangement. Exemplary techniques for determining and/or modifying the CWST include, but are not limited to, those disclosed in U.S. Pat. Nos. 4,954,256; 4,925,572 and 5,100,564, and International Publication No. WO 92/07656.

In a preferred embodiment, at least one fluid treatment element is hydrophilic, i.e., having a CWST greater than 72 dynes/cm. In one embodiment, the CWST may be in the range from about 75 to about 90 dynes/cm, or more.

In one embodiment, the fluid filtration arrangement may be surface modified by grafting thereon a hydroxyl-containing monomer to provide an element having a low affinity for amide or peptide-group containing materials, e.g., proteinaceous materials. Preferably, low affinity for proteinaceous materials refers to adsorption of less than about 100 micrograms per square centimeter of proteinaceous materials as measured by the Bovine Serum Albumin Adsorption test. The adsorption of proteinaceous material may be less than about 35 micrograms per square centimeter. One suitable technique for providing an element having a low affinity for proteinaceous materials is described in U.S. Pat. No. 4,906,374.

The fluid treatment arrangement treated to inactivate and/or kill microorganisms. For example, the arrangement may be rendered bacteriostatic or virustatic; or may be rendered virucidal or bacteriocidal, as is known in the art.

The fluid treatment arrangement may be fashioned in a variety of ways. For example, it may include one or more of the following: a web, a sheet, and a depth filter. The fluid treatment arrangement may be formed into any geometric shape or form suitable for passing a parenteral fluid therethrough. Preferably, the fluid treatment arrangement comprises at least one flat planar sheet, although in another embodiment, it may comprise at least one sheet formed into a pleated, corrugated, or accordion form.

The fluid treatment arrangement, which may be fibrous and/or membranous, may comprise a composite or a multilayer arrangement. Layers may be, for example, bonded, contiguous and/or separate. The fluid treatment arrangement may also include additional constituents, including, but not limited to at least one layer to provide support and/or better drainage. Exemplary supports and/or drainage components are non-woven polyester or polypropylene mesh.

The fluid treatment arrangement made in accordance with this invention may be preformed to controlled dimension, for example, to controlled thickness and controlled pore structure, in order to form a self-contained or unitary structure prior to assembly in a housing. The fluid treatment arrangement may be a preformed, integral structure. Suitable techniques for producing a preformed porous structure include those disclosed in U.S. Pat. Nos. 4,880,548 and 4,925,572.

A fluid treatment arrangement produced in accordance with the present invention preferably may have a flow area of about 40 cm² to about 2 cm². As used herein, the term flow area refers to the face surface area contacted by the parenteral fluid. In a more preferred embodiment, including a first fluid treatment element and a second fluid treatment element, one fluid treatment element has a flow area in the range of about 20.0 cm² to about 5.0 cm², more preferably about 10.0 cm²; and the other fluid treatment element has a flow area in the range of about 7.50 cm² to about 1.9 cm², more preferably about 3.8 cm².

A preferred relative voids volume for the fluid treatment arrangement may be in the range of about 50% to about 90%, more preferably in the range of from about 60% to about 80%. In a more preferred embodiment, including a first fluid treatment element and a second fluid treatment element, both elements have similar relative voids volumes.

The thickness of the fluid treatment arrangement may be in the range of, for example, from about 0.002 inches to about 0.020 inches, more preferably about 0.008 inches.

In other embodiments that may involve different flow rates and/or volumes of parenteral fluids, e.g., involving parenteral fluids for neonatals, the fluid treatment arrangement may be adjusted as necessary. For example, in those embodiments including passing a therapeutic parenteral fluid, e.g., including a drug and/or nutrient, through a fluid treatment element, and administering the therapeutic fluid to a neonatal, the element flow area may be reduced as compared to the element flow area for an older or larger patient.

Included within the scope of the present invention are the use of, for example, other pore ratings, pore sizes and/or arrangements of fibers and membranes, with respect to particular layers as well as throughout the fluid treatment arrangement. These alternatives may be chosen based on achieving a desired result, e.g., relating to the flow rate, the pressure drop, the type of fiber and/or membrane used, as well as other considerations.

The fluid processing apparatus according to the invention may include at least one, and more preferably at least two, vents or venting elements for use in moving gas to a desired location and/or separating gas from the fluid. In a more preferred embodiment, each subassembly 450, 460 includes at least two vents. In the embodiments illustrated in FIGS. 2, 4, 6 and 8, a plurality of vents 500 include openings 400 in the housing, each covered by a porous medium 600, so that gas or air may be displaced from the parenteral fluid flow path or separated from the fluid, and vented to the atmosphere. Preferably, as in the illustrated embodiments, the housing includes a well or depression, 70c or 70d, associated with each vent, and each depression communicates with at least one opening 400. For example, with respect to respect to FIGS. 1 and 2, subassembly 450 includes two vents 500, two wells or depressions 70c, two porous media 600, and each well or depression communicates with two openings 400. Similarly, subassembly 460 includes two vents 500, two wells or depressions 70d, two porous media 600, and each well or depression communicates with an opening 400. In a preferred embodiment, each depression 70c and 70d includes at least one, and more preferably at least two, ribs 80c facing the downstream side of the porous medium 600. In some embodiments, the use of ribs may provide for increased efficiency of gas flow by spacing the porous medium away from the bottom of the depression.

In a preferred embodiment, the vent includes porous medium 600, which is liquophobic, and, more preferably, hydrophobic, such that the porous medium is liquid-repellant or non-wettable by the parenteral fluid and which allows gas that may be present in the parenteral fluid and/or the fluid processing device to pass out of the device, for example, through opening 400. Preferably, the gas venting porous medium 600 comprises at least one microporous membrane. More preferably, the porous membrane is a membrane that allows gas to pass from the apparatus to the environment, while maintaining sterility, e.g., by blocking or preventing the entry of bacteria.

Preferably, the venting element vents gas from the system, in order to prime the device and eliminate any extraneous gas. This may be desirable since the presence of gas may reduce the efficiency of the fluid treatment arrangement, e.g., by blocking a fluid treatment element. More preferably, venting gas through the gas venting element prevents gas from reaching a patient.

As used herein, gas refers to any gaseous fluid, such as air, sterilized air, oxygen, carbon dioxide, and the like; it is intended that the invention is not to be limited thereby.

Figure 4:
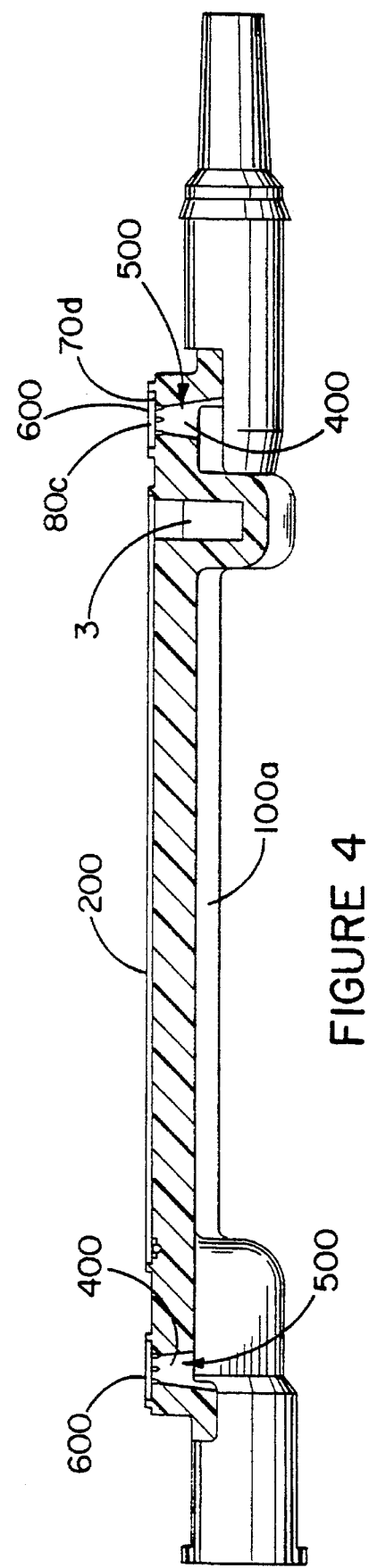
FIG. 4 is a cross-sectional elevated view taken along the line II—II of the device of FIG. 2.

In accordance with the invention, the vent may be located in a variety of configurations with respect to the flow of the parenteral fluid. Thus, the vent may be oriented according to an intended use. For example, the gas venting element may be located in any of the various components of the fluid processing apparatus or the administration system. By way of illustration, at least one gas venting element may be included in at least one of the conduits used to connect the various components of the administration system, in a wall of a parenteral fluid container, or in a port on or in one of the containers or the fluid processing apparatus. Generally, however, it is preferred to include the gas venting element within the apparatus or filter assembly. In a more preferred embodiment, wherein the venting element includes a porous medium 600, the porous medium may be located in the same plane as the fluid treatment arrangement, for example, as illustrated in FIGS. 2 and 4.

In a preferred embodiment, the fluid processing apparatus 10 includes two or more vents 500. In a more preferred embodiment, each subassembly, 450 and 460, includes at least one vent. In the illustrated embodiments, each subassembly 450 and 460 includes at least two vents 500, with at least one vent 500 near an entry port, e.g., 2 and/or 5, and 8, and at least one vent 500 near an exit port, e.g., 3 and 6.

Suitable vents, including gas outlets, and methods of using them include, but are not limited to, those disclosed in International Publication Nos. WO 93/22029 and WO 91/17809; and U.S. Pat. Nos. 5,252,222, 5,126,054, and 4,954,256.

The gas venting porous medium should have the necessary strength to handle the pressures encountered in use and have the ability to provide the desired permeability without the application of excessive pressure. For convenience, the gas venting porous medium will be referred to hereinafter as the "gas venting membrane", or the "membrane", although the invention is not to be so limited.

The gas venting membrane may be produced from any suitable material which is compatible with the parenteral fluid. Preferably, the material is commercially available. The membrane may be formed, for example, from the materials listed above with respect to the fluid treatment arrangement. Preferred polymers are polyolefins, polyesters, polyamides, polyurethanes, polysulfones, and fluoropolymers such as polyvinylidene difluoride, polytetrafluoroethylene, and perfluoroalkoxy resins. Particularly preferred are fluoropolymers, more preferably, polytetrafluoroethylene (PTFE).

The membrane may be untreated, or treated or modified to make it more effective, e.g., liquophobic. A liquophobic gas venting membrane in the context of this invention is one that has a critical wetting surface tension lower than the surface tension of the parenteral fluid, or is not readily or spontaneously wetted by the parenteral fluid. Because the liquophobic membrane is not wettable, or poorly wettable, by the parenteral fluid being treated or processed in the system, gas in the system that contacts the liquophobic membrane may pass through it, while the parenteral fluid may not.

The gas venting membrane may be treated to increase its liquophobicity. For example, the membrane may be surface modified to decrease the critical wetting surface tension (CWST), with the term CWST being as defined above with respect to the fluid treatment arrangement. In one embodiment, the gas venting membrane may have a CWST of less than about 28 dynes/centimeter, rendering it liquid-repelling or non-wetting by liquids with surface tensions well below that of water's surface tension of 72 dynes/centimeter.

Surface characteristics of the gas venting membrane may be modified by a number of methods, including those described above with respect to the fluid treatment arrangement.

In a preferred embodiment of the gas venting membrane according to the subject invention, the membrane may comprise an untreated PTFE microporous membrane commercially available from, for example, W. L. Gore Associates, Inc.

In another embodiment of the gas venting membrane of the subject invention, the membrane may be surface modified by bonding thereon one or more fluorine-containing monomers, for example, as described in U.S. Pat. No. 4,954,256.

The selected pore structure, e.g., pore rating, of the gas venting membrane may effectively preclude wetting at the operating pressures utilized for processing the parenteral fluid. With respect to pore structure, since the gas venting membrane may be open to the atmosphere to allow the gas to be vented, which could allow bacteria to enter, the pore structure, e.g., the pore rating, should be selected to preclude bacteria from entering the system or contacting the parenteral fluid. For example, the bacterial blocking pore rating of the gas venting element should be about 0.3 micrometers or less, more preferably in the range of about 0.2 to about 0.02 micrometers.

The gas venting membrane may include two or more layers. The membrane may include additional constituents, including, but not limited to, at least one liquophilic layer and/or at least one layer to provide support. As with the fluid treatment arrangement, the layers of the gas venting membrane may be individually prepared and bonded together by various means known to those skilled in the art.

The housing may be fabricated from any suitably rigid, impervious material, including any impervious thermoplastic material, which is compatible with the fluid being processed. For example, the housing may be fabricated from a metal, such as stainless steel, or from a polymer. In a preferred embodiment, the housing is fabricated by injection molding from a polymer, more preferably a transparent or translucent polymer, such as an acrylic, polypropylene, polystyrene, or a polycarbonated resin. Such a housing is easily and economically fabricated, and allows observation of the passage of the liquid through the housing.

In some embodiments, the housing may be constructed of diethylhexylphthalate (DEHP) free and/or phthalate free material.

The surfaces of the housing contacting the fluid may be treated or untreated. For example, the surfaces of the housing contacting the fluid may be rendered liquophilic for better priming. Methods for treating the surface of the housing include but are not limited to radiation grafting and gas plasma treatment.

The housing may be configured for ease of use. For example, the housing may be curved and/or include a bracket for ease of mounting or support during administration of the parenteral fluid.

The fluid treatment arrangement 200 may be sealed within the housing to achieve convenience of use, rapid priming, and, in a preferred embodiment, efficient air clearance. For example, the fluid treatment arrangement may be compression sealed or interference fit within the housing. The fluid treatment arrangement may be bonded to the housing. Suitable methods for sealing, fitting, and/or bonding the arrangement within or to the housing are known in the art. Preferably, the fluid treatment arrangement is welded to the housing, e.g., heat welded or ultrasonically welded.

In a preferred embodiment wherein the fluid treatment arrangement 200 includes two or more fluid treatment elements 200a and 200b, at least one portion of the housing, e.g, 100b, includes at least one sacrificial ridge, such as a boss, bead, or rib (not to be confused with ribs 80a, 80b, or 80c) located to contact the edges of the fluid treatment elements 200a and 200b when the portions of the housing are sealed together. These ridges (not shown) may be bonded to the fluid treatment elements, e.g., near the periphery of the elements, to provide for a fluid tight seal. Preferably, the ridge is welded to the membrane. In a preferred embodiment, there is a separate sacrificial ridge surrounding the perimeter of each of depression 70a and 70b. Other suitable techniques for sealing or fitting the medium within the housing are included within the scope of the invention.

In those embodiments including a vent, the vent may be sealed or fitted within the housing as noted above with respect to the fluid treatment arrangement. In a more preferred embodiment, the vent includes at least one gas venting membrane, and the membrane is bonded, e.g., welded, to a ridge as described above. As with the fluid treatment arrangement, in a preferred embodiment, a ridge surrounds the perimeter of each of depressions 70c and 70d.

While separate fluid treatment elements may be individually placed within the housing, e.g., along flow paths 50 and 60, in a preferred embodiment, a fluid treatment arrangement is placed in the housing along both flow paths, and this fluid treatment arrangement is then sectioned or divided as desired to provide two or more fluid treatment elements and two or more separate and isolated fluid flow paths. For example, a fluid treatment arrangement 200 may be placed on housing 100a and mounted thereto, spanning both wells 70a and 70b and groove 130. For example, fluid treatment element may be welded to ridges that surround depressions 70a and 70b, respectively. Once mounted, the fluid treatment arrangement 200 may be divided to form first fluid treatment element 200a and second fluid treatment element 200b to provide separate fluid treatment flow paths through the housing.

In one embodiment, fluid treatment arrangement 200 is slit longitudinally, e.g., along the groove 130 so that the edges of the elements 200a and 200b may be sealed when spacer 120 from housing portion 100b fits into groove 130 of housing portion 100a. Preferably, this embodiment includes slots in the housing portion 100a between groove 130 and wells 70a, 70b so that portions of the elements 200a, 200b may be tucked into the slots after the fluid treatment arrangement is slit and the fluid treatment arrangement is welded to the ribs of the housing.

In a less desirable embodiment, the fluid treatment element remains uncut, and housing portions 100a and 100b may be sealed in such a fashion that separate and isolated flow paths are provided. For example, spacer 120 may be compressed against fluid treatment element 200 such that flow path 50 is isolated from flow path 60, with or without the spacer fitting into a channel formed in housing portion 100a.

In those embodiments including at least one vent including at least one gas venting membrane, separate membranes may be individually placed in the housing, e.g., to cover depressions 70c and 70d. Alternatively, a single membrane may cover depressions 70c and 70d near the inlet and/or the outlet portions of the housing, and this membrane may be sectioned or divided as desired to provide two or more venting elements. The gas venting membrane may be divided, slit or sealed as described above with respect to the fluid treatment arrangement. In a preferred embodiment, a first membrane covers depressions 70c and 70d near the inlet end of the housing, and a second membrane covers depressions 70c and 70d near the outlet end of the housing, and the membranes are slit along groove 130 and tucked into slots in the housing portion 100a between groove 130 and wells 70c and 70d.

Figure 7:
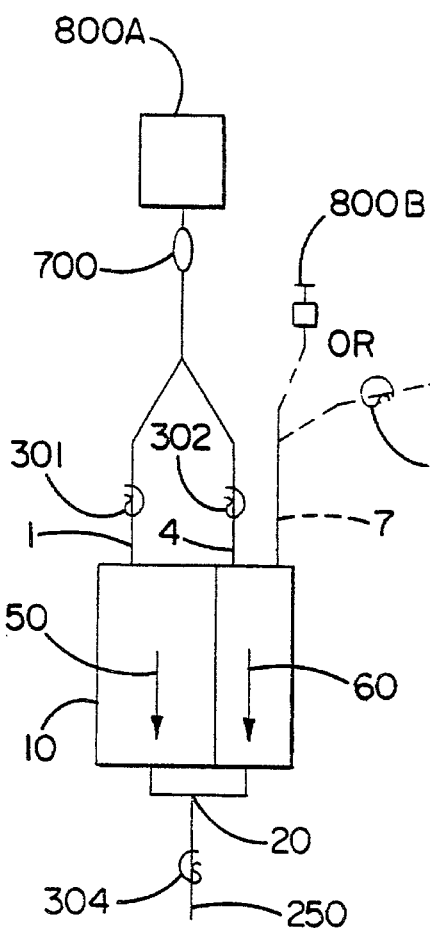
FIG. 7 is an embodiment of a parenteral fluid processing system according to the invention.

The filter assembly, i.e., the housing including the fluid treatment arrangement, may be incorporated into a fluid processing and/or administration system. Accordingly, the system may include, for example, at least one container, conduit, injection port, gas inlet, connector, drip chamber and/or flow control device. The exemplary systems illustrated in FIGS. 7 and 9 include a drip chamber 700, and at least one container, 800A. The system illustrated in FIG. 7 includes additional containers, e.g. 800B or 800C. In one embodiment, as illustrated in FIG. 7, one of the containers, i.e., 800B, is a syringe. According to the embodiment illustrated in FIG. 9, a second parenteral fluid, e.g., from another container, may be added through access port 150.

The containers and/or conduits which may be used in accordance with the invention may be constructed of any material compatible with a fluid such as a parenteral fluid. The composition of the container and conduit may vary with the nature of the parenteral fluid or fluids utilized. A wide variety of suitable containers and conduits are already known in the art. Exemplary containers include, but are not limited to, a syringe or a flexible bag. Typical conduits include for example, those constructed of PVC. In some embodiments, the containers and/or conduits are constructed of diethylhexylphthalate (DEHP) free and/or phthalate free material. It is intended that the invention should not be limited by the type or composition of the container and/or conduit being employed.

In some embodiments, at least one flow control device such as a clamp, seal, stopcock, valve, transfer leg closure, or the like may be used to facilitate a desired function, i.e., to establish a desired flow path for parenteral fluid and/or gas. For example, in the embodiments shown in FIGS. 7 and 9, the system includes flow control devices such as clamps 300, 301, 302, 303, and 304.

Figure 9:
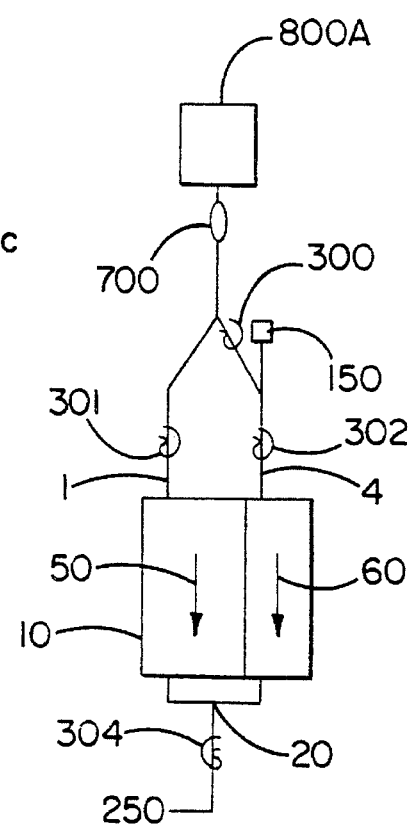
FIG. 9 is another embodiment of a parenteral fluid processing system according to the invention.

In preferred embodiments, as illustrated in FIGS. 7 and 9, the system includes at least one drip chamber 700, preferably located upstream of the fluid processing apparatus 10. A variety of suitable drip chambers are already known in the art.

The system may include additional components, such as, for example, an administration pump.

Fluids may be processed in accordance with the invention for any suitable length of time. For example, parenteral fluids may be passed through the fluid treatment arrangement and administered to a patient for 24 hours to 96 hours, or more, without replacing the fluid processing apparatus 10. In accordance with the invention, parenteral fluid or fluids may be passed through the fluid processing apparatus and administered to a patient over a short period a time, e.g., to provide a bolus dose for several minutes, and/or fluid may be administered over a longer period, e.g., to provide a continuous, maintenance or sedative dose over several days.

In a more preferred embodiment, involving the administration of first and second parenteral fluids to a patient, a method in accordance with the invention includes administering a small volume or a bolus dose of one of the parenteral fluids, and administering a larger volume or dose of the other parenteral fluid. In accordance with the invention, the small volume or dose of one parenteral fluid is administered efficiently, e.g., quickly and accurately, and then the other parenteral fluid may be administered with a minimum of delay.

In accordance with the invention, for example, using FIGS. 2 and 6 for reference, a parenteral fluid such a saline may be processed (e.g., passed through one flow path such as flow path 50) and administered for several hours to several days, and another parenteral fluid such as a drug may be processed (e.g., passed through a separate flow path such as flow path 60) for a lesser amount of time. In another embodiment, a first therapeutic fluid is passed through flow path 50, and a second, different, therapeutic fluid is passed through separate flow path 60. Typically, the flow of the first parenteral fluid through flow path 50 is stopped, while a second parenteral fluid is passed through flow path 60 and administered for a desired length of time, for example, several minutes to several hours.

Preferably, since some second parenteral fluid may remain in, for example, the housing, the second fluid treatment element 200b, and/or the downstream conduit, this remaining second parenteral fluid may be recovered, e.g., flushed and administered to the patient, by passing additional first parenteral fluid through flow path 60. For example, additional first parenteral fluid may be passed from an upstream container through second subassembly 460 to flush retained second parenteral fluid into conduit 250 and then the patient.

In those embodiments where it may be desirable to resume the administration of the first parenteral fluid after administration of the second parenteral fluid, e.g., protocols including long term fluid replenishment, the flow through flow path 60 may be stopped, and the flow through flow path 50 may be resumed.

In a typical protocol, a first parenteral fluid, e.g., a carrier fluid such as saline, is passed through first fluid inlet 1 and second fluid inlet 4, and along separate and isolated flow paths 50 and 60, and through fluid treatment elements 200a and 200b of the fluid treatment arrangement 200 and through the outlet 20 to prime the fluid processing apparatus.

For example, with respect to flow path 50, in the embodiment shown in FIGS. 5 and 6, used in the exemplary system shown in FIG. 7, after a source of parenteral fluid in container 800A is placed in fluid communication with apparatus 10, clamps 301 and 304 are opened, and clamp 302 is closed, and the method includes passing first parenteral fluid through first fluid inlet 1 into first subassembly 450. Optionally, for example, in those embodiments including the use of container 800C, clamp 303 may be used, and is closed before passing the parenteral fluid through the apparatus 10. Fluid passing through inlet 1 passes through first fluid entry port 2, into first chamber 110a, and through first fluid treatment element 200a. Fluid passing through first fluid treatment element 200a is passed along channels 90a and into well or depression 70a and then through first fluid exit port 3. Fluid is passed out of first subassembly 450 by passing the fluid through first fluid exit port 3 into outlet 20 and conduit 250.

In a similar manner with respect to flow path 60, clamp 302 is opened and clamp 303 (if present) remains closed, and the method includes passing first parenteral fluid through second fluid inlet 4 into second subassembly 460. Fluid passing through inlet 4 passes through second fluid entry port 5, into second chamber 110b, and through second fluid treatment element 200b. Fluid passing through second fluid treatment element 200b is passed along channels 90b and into well or depression 70b and into fluid exit port 6. Fluid is passed out of second subassembly 460 by passing the fluid through fluid exit port 6 into outlet 20 and conduit 250. The method may include passing first parenteral fluid through flow path 50 (e.g., through first subassembly 450) and flow path 60 (e.g., through second subassembly 460) sequentially, or contemporaneously.

In a more preferred embodiment, the method includes passing parenteral fluid through separate and isolated fluid flow paths through first subassembly 450 and second subassembly 460 and venting air or gas from the fluid processing apparatus 10 by passing the air through at least one vent 500 before administering the fluid. For example, parenteral fluid may be passed along separate and isolated flow paths 50 and 60 as described above. Illustratively, clamp 303 (if present) is closed, clamp 304 is opened, and clamps 301 and 302 are opened, sequentially or contemporaneously. First parenteral fluid is passed through first fluid inlet 2 and second fluid inlet 4 into first subassembly 450 and second subassembly 460, respectively, and then gas is vented through vent 500, e.g., by passing gas through membrane 600, into depression 70c or 70d, and then through opening 400. Preferably, while venting gas, the housing is positioned to improve the efficiency of venting. For example, during venting, the apparatus is preferably positioned so that outlet 20 points upwardly and inlets 1 and 4 point downwardly. During venting the apparatus may be tapped gently to dislodge air bubbles while the outlet 20 points upwardly.

Figure 8:
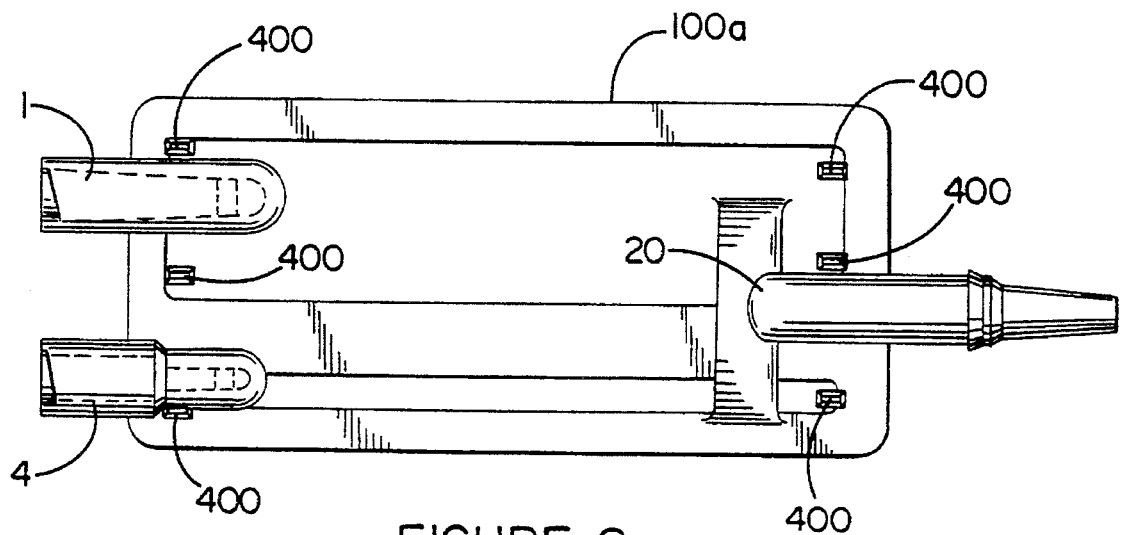
FIG. 8 is a bottom plan of the housing of the device of FIG. 1.

As shown, for example, in FIGS. 4 and 8, vents 500 may be located with respect to fluid processing apparatus 10 so that venting occurs regardless of the position of the device. With respect to FIG. 4, regardless of the position or orientation of the device, gas present in subassemblies 450 and/or 460 should pass through at least one vent 500 located in each subassembly.

One gas has been vented, outlet 20 may be returned to a downward position, and first parenteral fluid may be passed through the subassemblies 450 and 460 and then passed through outlet 20 and conduit 250.

The embodiment illustrated in FIGS. 1 and 2 utilized in, for example, the system illustrated in FIG. 9 may be employed in a similar manner. For example, after a source of parenteral fluid is placed in fluid communication with apparatus 10, clamps 300 and 301 may be opened, and first parenteral fluid may be passed along separate and isolated flow paths 50 and 60 as noted above, e.g., with respect to first and second subassemblies 450 and 460. Optionally, an additional clamp, clamp 302 may also be included in the system, and this clamp will be opened before passing the fluid along flow path 60.

Illustratively, first parenteral fluid is passed through first fluid inlet 1 into first subassembly 450. Fluid passing through inlet 1 passes through first fluid entry port 2, into first chamber 110a, and through first fluid treatment element 200a. Fluid passing through first fluid treatment element 200a is passed along channels 90a and into well or depression 70a and then through first fluid exit port 3. Fluid is passed out of first subassembly 450 by passing the fluid through first fluid exit port 3 into outlet 20 and conduit 250. With respect to subassembly 460, first parenteral fluid is passed through second fluid inlet 4 into second subassembly 460. Fluid passing through inlet 4 passes through second fluid entry port 5, into second chamber 110b, and through second fluid treatment element 200b. Fluid passing through second fluid treatment element 200b is passed along channels 90b and into well or depression 70b and into fluid exit port 6. Fluid is passed out of second subassembly 460 by passing the fluid through fluid exit port 6 into outlet 20 and conduit 250.

If desired, clamp 301 may be closed before passing fluid through second subassembly 460. In those embodiments including venting, gas may be passed through vent 500 as described above.

Preferably, the primed fluid processing apparatus may be attached to the patient, e.g., via a cannula or a catheter, and/or the first and second parenteral fluids may be administered as desired. Typically, using FIGS. 7 and 9 for reference, clamps 300 and 302 may be closed initially, while clamps 301 and 304 are open, and first parenteral fluid may be passed through first subassembly 450 and fluid flow path 50 and administered, e.g., infused. In a preferred embodiment, the first parenteral fluid is a carrier fluid such as saline, and it may be passed through inlet 1, through first subassembly 450 and common outlet 20, and administered to a patient.

The second parenteral fluid, which may be in a container, e.g., 800B or 800C, as illustrated in FIG. 7, may be placed in fluid communication with apparatus 10 through supplementary fluid inlet 7. Alternatively, for example, with respect to FIG. 9, a second parenteral fluid may be placed in fluid communication with apparatus 10 through access port 150.

With respect to the second fluid, although it is possible to process two or more fluids concurrently, preferably, using FIG. 9 for reference, clamps 300 and 301 are closed before administering the second parenteral fluid through second subassembly 460 and fluid flow path 60. Preferably, the second fluid is a different parenteral fluid than the first parenteral fluid. In a more preferred embodiment, the second parenteral fluid includes a drug, which may be infused, or more preferably, injected, into the patient. For example, with respect to FIG. 7, parenteral fluid in a container 800C may be infused to a patient through apparatus 10 after opening clamp 303. In a more preferred embodiment, parenteral fluid in a container 800B may be injected to the patient through the apparatus. Similarly, with respect to FIG. 9, parenteral fluid may be injected or infused to the patient through apparatus 10 via access port 150 after closing clamp 300, and opening optional clamp 302.

In those more preferred embodiments involving administering a small volume and/or a bolus dose of the second parenteral fluid, for example, to a neonatal patient, the method preferably includes minimizing the amount of amount of fluid that is "lost" to the fluid treatment arrangement and/or held up in the housing while passing the fluid through second subassembly 460. For example, since second subassembly 460 may be smaller than first subassembly 450, and/or second fluid treatment element 200b may be smaller than first fluid treatment element 200a, passing the second parenteral fluid through subassembly 460 may provide for decreasing the fluid lost and/or held up, and thereby provide a full dose to the patient.

With respect to the embodiment illustrated in FIGS. 5 and 6, which includes a separate fluid entry port, as utilized in, for example, the system illustrated in FIG. 7, clamps 301 and 302 are closed, and second parenteral fluid is passed through supplementary fluid inlet 7 into second subassembly 460 and along separate and isolated flow path 60. In those embodiments including a container 800C rather than a syringe, clamp 303 is opened before passing the second parenteral fluid through supplementary inlet 7. The method includes passing second parenteral fluid through supplementary fluid inlet 7 through supplementary fluid entry port 8 into chamber 110b. The second parenteral fluid may then be passed through primed second fluid treatment element 200b of fluid treatment arrangement 200, along channels 90b, into well or depression 70b, and through exit port 6 and out of second fluid subassembly 460, e.g., into outlet 20 as noted above with respect to priming with the first parenteral fluid. Preferably, the fluid is administered, and the flow may then be stopped.

In those embodiments including an access port (e.g., FIGS. 1, 2 and 9) instead of a separate fluid entry port (e.g., FIGS. 5, 6, and 7), clamp 300 may be closed, and the second parenteral fluid may be passed through access port 150, through conduit 180 and into second subassembly 460 through second fluid entry port 5. The method may include passing second parenteral fluid through second fluid entry port 5 into second chamber 110b, through second fluid treatment element 200b of the fluid treatment arrangement 200, through exit port 6, and into outlet 20. Typically, before administering the second parenteral fluid, clamp 301 (on conduit 170 upstream of first fluid inlet 1) is closed, and second parenteral fluid may be passed through flow path 60 and administered, and the flow may then be stopped.

In some embodiments, for example, including administration of a small volume and/or a bolus dose of the second parenteral fluid, once the flow of the second parenteral fluid has been stopped, it may be desirable to flush the remaining second parenteral fluid so that the entire volume and/or dose may be delivered to the patient. Typically, with respect to the embodiment illustrated in FIGS. 5, 6, and 7, clamp 303 (if present) is closed, and clamp 302 is opened, and additional first parenteral fluid is passed through second fluid path 60 (e.g., through inlet 4, inlet port 5, fluid treatment element 200b, and outlet port 6) until the desired volume and/or dose of second parenteral fluid is delivered to the patient.

With respect to FIGS. 1, 2 and 9, typically, clamp 301 is closed and clamp 300 is opened, and first parenteral fluid is passed through the second fluid path 60 (e.g., through inlet 4, inlet port 5, fluid treatment element 200b, and outlet port 6) until the desired volume and/or dose of second parenteral fluid is delivered to the patient.

In those embodiments including additional administration of the first parenteral fluid, clamp 302 (in FIG. 7) or clamp 300 (in FIG. 9) may remain open, and first parenteral fluid may continue to pass through second flow path 60. Typically, however, these clamps may be closed, and clamp 301 may be opened, so that first parenteral fluid may be passed through first flow path 50. This may be desirable for those protocols that may include additional administration of the second parenteral fluid. This may also be desirable for those protocols including administration of larger volumes of the first parenteral fluid, particularly when one section of the fluid treatment arrangement 200, e.g., 200b, may be smaller than the other section.

In an alternate embodiment (not shown), at least one valve such as a check valve may be used to prevent flow into first subassembly 450, so that second parenteral fluid may be passed into second subassembly 460 at the desired time. For example, in a variation of the embodiment illustrated in FIGS. 1 and 9, a check valve may be interposed between connector 190 and access port 150 while eliminating clamp 300. Preferably, the check valve is positioned to prevent flow in the direction from conduit 180 and/or second fluid inlet 4 toward connector 190 and/or conduit 160, but to allow flow in the other direction. In this embodiment, as second parenteral fluid is added through access port 150, the check valve prevents backflow into conduit 160 and/or first inlet 1. Once the addition of second parenteral fluid through access port 150 is completed, flow of first parenteral fluid through conduit 160 into conduit 180 and second subassembly 460 may be resumed, manually or automatically.

In some embodiments, a drip chamber may be interposed between at least one source of a parenteral fluid and an inlet, so that, for example, the flow rate may be monitored. As illustrated in FIG. 7, the flow rate during administration of a first parenteral fluid to a patient may be monitored as the parenteral fluid passed from a container 800A through a drip chamber and into device 10 via inlet 1. In some embodiments, a drip chamber may be utilized during administration of the second parenteral fluid to the patient. For example, with respect to FIG. 7, a drip chamber may be interposed between container 800C and device 10 so that the flow rate of the second parenteral fluid may be monitored.

In other embodiments, at least one additional fluid may be passed through one of the flow paths. For example, a third parenteral fluid may be passed through fluid flow path 60 and administered to a patient.

In one embodiment, at least one parenteral fluid may be passed in a reverse direction through the fluid treatment arrangement 200 to provide efficient priming at a desired time. For example, parenteral fluid may be passed in one direction through first fluid treatment element 200a (e.g., through inlet 1, through element 200a and then through exit port 3 into outlet 20), and a parenteral fluid may be passed in the other direction through second fluid treatment element 200b (e.g., through outlet 20, exit port 6, then through second fluid treatment 200b and entry port 5 and inlet 4). This may be desirable in some embodiments wherein one fluid flow path, e.g., fluid flow path 60, might not be used for a period of time.

Illustratively, it might be desirable to utilize first fluid flow path 50 soon, e.g., to provide immediate fluid replenishment to the patient using first subassembly 450, while second fluid flow path 60 (e.g., providing medication for the patient using subassembly 460) may be utilized later. In accordance with the invention, a parenteral fluid may be passed along first fluid flow path 50 as described above. For example, parenteral fluid may be passed through first inlet 1 through first fluid treatment element 200a and first exit port 3 into outlet 20, and gas may be passed through the gas venting membrane 600 and opening 400 as described above. Parenteral fluid may be passed through outlet 20 into conduit 250 and administered to a patient. However, there is no need to pass parenteral fluid along second fluid flow path 60 at this time.

At the appropriate time, parenteral fluid may be passed from outlet 20 through second fluid treatment element 200b to prime the element 200b. For example, parenteral fluid, e.g., saline, may be passed through outlet 20, fluid exit port 6, second fluid treatment element 200b and into fluid entry port 5 and/or supplementary entry port 8. Gas may be passed through gas venting membrane 600 and opening 400. Second parenteral fluid may then be added, e.g., through supplementary fluid inlet 7 or access port 150. This fluid may be passed along second fluid flow path 60, e.g., through inlet entry port 5 or supplementary entry port 8, and then through second fluid treatment element 200b, through exit port 6 and outlet 20, and administered to the patient.

In a preferred embodiment, the fluid passing from outlet 20 through fluid treatment element 200b is first passed along fluid flow path 50. For example, with respect to FIG. 9, clamp 304 may be closed to allow some fluid that had passed along fluid path 50 to pass in the opposite direction along fluid flow path 60. In another embodiment, a separate source of parenteral fluid may be used, and this fluid may added, for example, using an access port connected to conduit 250, so that this fluid may be passed through the outlet 20 and toward inlet port 5 and/or 8.

While the invention has been described in some detail by way of illustration and example, it should be understood that the invention is susceptible to various modifications and alternative forms, and is not restricted to the specific embodiments set forth. It should be understood that these specific embodiments are not intended to limit the invention but, on the contrary, the intention is to cover all modifications, equivalents, and alternatives falling within the spirit and scope of the invention.

We claim:

1. A method for treating parenteral fluid comprising:

passing a first parenteral fluid through a first fluid flow path through a porous fluid treatment arrangement;

passing a second parenteral fluid through a separate and isolated second fluid flow path through the porous fluid treatment arrangement; and, passing additional first parenteral fluid through the separate and isolated second fluid flow path through the porous fluid treatment arrangement.

2. The method of claim 1 wherein passing the first parenteral fluid through the first fluid flow path includes passing the first parenteral fluid through a first porous fluid treatment element of the porous fluid treatment arrangement; and, wherein passing the second parenteral fluid through the separate and isolated second fluid flow path includes passing the second parenteral fluid through a second porous fluid treatment element of the porous fluid treatment arrangement.

3. The method of claim 2 including passing the second parenteral fluid through a second porous fluid treatment element having a hold up volume of less than about 0.9 cc.

4. The method of claim 2 wherein passing the first parenteral fluid through the first porous fluid treatment element comprises passing the fluid through an element having an effective flow area of about 10 cm$^2$ or less; and passing the second parenteral fluid through the second porous fluid treatment element comprises passing the fluid through an element having an effective flow area of about 3.8 cm$^2$ or less.

5. The method of claim 2 wherein the first porous fluid treatment element comprises at least one membrane, and the second porous fluid treatment element comprises at least one membrane.

6. The method of claim 5 wherein the first porous fluid treatment element comprises at least one membrane having a pore rating in the range of about 0.45 to about 0.2 micrometers, and the second porous fluid treatment element comprises at least one membrane having a pore rating in the range of about 0.45 to about 0.2 micrometers.

7. The method of claim 2 wherein passing the second parenteral fluid through the separate and isolated second fluid flow path holds up less fluid than passing the first parenteral fluid through the first fluid flow path.

8. The method of claim 2 wherein passing the first parenteral fluid through the first fluid flow path holds up about 2.4 cc or less of fluid; and passing the second parenteral fluid through the separate and isolated second fluid flow path holds up about 0.6 cc or less of fluid.

9. The method of claim 1 wherein passing the second parenteral fluid through the separate and isolated second fluid flow path holds up less fluid than passing the first parenteral fluid through the first fluid flow path.

10. The method of claim 1 wherein the porous fluid treatment arrangement includes a porous fluid treatment element sectioned to provide said first fluid flow path and said separate and isolated second fluid flow path, so that passing the first parenteral fluid and the second parenteral fluid therethrough holds up less fluid in the separate and isolated second flow path than in the first flow path.

11. The method of claim 10 wherein passing the first parenteral fluid through the first fluid flow path holds up about 2.4 cc or less of fluid; and passing the second parenteral fluid through the separate and isolated second fluid flow path holds up about 0.6 cc or less of fluid.

12. The method of claim 1 wherein a first subassembly includes the first fluid flow path and a second subassembly includes the separate and isolated second flow path; the method including:

passing the first parenteral fluid through the first subassembly;

passing the second parenteral fluid through the second subassembly; and, passing additional first parenteral fluid through the second subassembly.

13. The method of claim 12 including passing the second parenteral fluid through the second subassembly having a hold up volume of less than about 0.9 cc.

14. The method of claim 1 further comprising administering the first parenteral fluid and the second parenteral fluid to a patient.

15. The method of claim 1 further comprising displacing gas from the first fluid flow path of the first parenteral fluid and displacing gas from the separate and isolated second fluid flow path of the second parenteral fluid.

16. The method of claim 15 wherein displacing gas from the first fluid flow path of the first parenteral fluid includes passing the gas through at least one gas venting porous medium communicating with the first fluid flow path; and wherein displacing gas from the separate and isolated second fluid flow path of the second parenteral fluid includes passing the gas through at least one gas venting porous medium communicating with the second fluid flow path.

17. The method of claim 1 wherein the porous fluid treatment arrangement comprises at least one membrane.

18. The method of claim 17 wherein the membrane has a pore rating in the range of about 0.45 to about 0.2 micrometers.

19. The method of claim 18 wherein the membrane has a negative zeta potential.

20. An apparatus for processing parenteral fluid comprising:

a porous fluid treatment arrangement;

a housing providing for at least a first fluid flow path from a first inlet through the porous fluid treatment arrangement and through a common outlet, and a separate and isolated second fluid flow path through a second inlet through the porous fluid treatment arrangement and through the common outlet;

wherein the porous fluid treatment arrangement is located within the housing, across the first fluid flow path and the separate and isolated second fluid flow path, said porous fluid treatment arrangement having a larger effective flow area along the first fluid flow path than along the second fluid flow path.

21. The apparatus of claim 20 wherein the porous fluid treatment arrangement includes a porous fluid treatment element sectioned to provide said first fluid flow path and said separate and isolated second fluid flow path.

22. The apparatus of claim 20 wherein the porous fluid treatment arrangement includes a first porous fluid treatment element located across the first fluid flow path, and a second porous fluid treatment element located across the separate and isolated second fluid flow path.

23. The apparatus of claim 22 wherein the first porous fluid treatment element includes an effective flow area of about 10 cm$^2$ or less; and the second porous fluid treatment element includes an effective flow area of about 3.8 cm$^2$ or less.

24. The apparatus of claim 20 wherein the second fluid flow path through the porous fluid treatment arrangement includes a hold up volume of about 0.9 cc or less.

25. The apparatus of claim 20 including at least one porous gas venting element communicating with the first fluid flow path, and at least one porous gas venting element communicating with the separate and isolated second fluid flow path.

26. The apparatus of claim 20 wherein the porous fluid treatment arrangement includes a effective flow area in the first fluid flow path in the range of about 20 cm$^2$ to about 5 cm$^2$; and an effective flow area in the separate and isolated second fluid flow path in the range of about 7.5 cm$^2$ to about 1.8 cm$^2$.

27. The apparatus of claim 26 wherein the effective flow area in the first fluid flow path is about 10 cm$^2$ to about 5 cm$^2$; and the effective flow area in the separate and isolated second fluid flow path is about 3.8 cm$^2$ to about 1.8 cm$^2$.

28. The apparatus of claim 20 further comprising an injection port in fluid communication with the apparatus.

29. The apparatus of claim 20 further comprising a single channel conduit integrally connected to the outlet.

30. The apparatus of claim 20 wherein the porous fluid treatment arrangement comprises at least one membrane.

31. The apparatus of claim 30 wherein the membrane has a negative zeta potential and a pore rating in the range of about 0.45 to about 0.2 micrometers.

32. The apparatus of claim 20, having about 70% of the total hold up volume along with the first fluid flow path, and about 30% of the total hold up volume along the second fluid flow path.

33. An apparatus for processing parenteral fluid comprising:

a housing including at least a first subassembly and a second subassembly;

said housing providing for at least a first fluid flow path through the first subassembly and a separate and isolated second fluid flow path through the second subassembly, said first subassembly having a larger fluid hold up volume than said second subassembly; and, a porous fluid treatment arrangement located within the first subassembly and the second subassembly, said arrangement interposed across the first fluid flow path and the separate and isolated second fluid flow path.

34. The apparatus of claim 33 wherein the porous fluid treatment arrangement within the first fluid flow path has a larger effective flow area than the porous fluid treatment arrangement within the separate and isolated second fluid flow path.

35. The apparatus of claim 34 wherein the porous fluid treatment arrangement comprises at least one membrane, said membrane having a negative zeta potential and a pore rating in the range of about 0.45 to about 0.2 micrometers.

36. The apparatus of claim 33 wherein the first subassembly includes a first chamber upstream of the porous fluid treatment arrangement and the second subassembly includes a second chamber upstream of the porous fluid treatment arrangement.

37. The apparatus of claim 33 including at least one porous gas venting element communicating with the first fluid flow path, and at least one porous gas venting element communicating with the separate and isolated second fluid flow path.

38. The apparatus of claim 33 wherein the porous fluid treatment arrangement comprises at least one membrane.

39. The apparatus of claim 33 wherein the first subassembly holds up about 70% of the total hold up volume of the apparatus, and the second subassembly holds up about 30% of the total hold up volume of the apparatus.

40. A method for processing parenteral fluid comprising:

passing a carrier fluid through a first fluid flow path through a porous fluid treatment arrangement; and, passing a therapeutic fluid including a lipid in emulsion, said therapeutic fluid being compatible with the carrier fluid, through a separate and isolated second fluid flow path through the porous fluid treatment arrangement, and passing additional carrier fluid through the separate and isolated second fluid flow path through the porous fluid treatment element.

41. The method of claim 40 including passing the carrier fluid and the therapeutic fluid through a common channel downstream of the porous fluid treatment arrangement.

42. The method of claim 41 wherein passing the therapeutic fluid through the common channel downstream of the porous fluid treatment arrangement comprises commingling the therapeutic fluid with the carrier fluid.

* * * * *